(12) United States Patent
Pathak et al.

(10) Patent No.: US 10,159,432 B1
(45) Date of Patent: Dec. 25, 2018

(54) DETECTION AND EVALUATION OF TASK PERFORMANCE WITH A HANDHELD TOOL

(71) Applicant: VERILY LIFE SCIENCES LLC, Mountain View, CA (US)

(72) Inventors: Anupam Pathak, Mountain View, CA (US); Ali Shoeb, Mill Valley, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 112 days.

(21) Appl. No.: 14/746,649

(22) Filed: Jun. 22, 2015

(51) Int. Cl.
| | |
|---|---|
| *A61B 5/11* | (2006.01) |
| *G01P 15/02* | (2013.01) |
| *G01B 21/00* | (2006.01) |
| *G01P 3/00* | (2006.01) |
| *A61B 5/00* | (2006.01) |

(52) U.S. Cl.
CPC .......... *A61B 5/1125* (2013.01); *A61B 5/1112* (2013.01); *A61B 5/4082* (2013.01); *A61B 5/4519* (2013.01); *A61B 5/6887* (2013.01); *A61B 5/7246* (2013.01); *A61B 5/7282* (2013.01); *G01B 21/00* (2013.01); *G01P 3/00* (2013.01); *G01P 15/02* (2013.01); *A61B 2560/0462* (2013.01); *A61B 2560/0475* (2013.01); *A61B 2562/0219* (2013.01)

(58) Field of Classification Search
CPC ............................. A61B 5/1125; A61B 5/4082
See application file for complete search history.

(56) References Cited

U.S. PATENT DOCUMENTS

| | | |
|---|---|---|
| 6,234,045 B1 | 5/2001 | Kaiser |
| 6,238,384 B1 | 5/2001 | Peer |
| 6,730,049 B2 | 5/2004 | Kalvert |
| 6,740,123 B2 | 5/2004 | Davalli et al. |
| 7,883,479 B1 | 2/2011 | Stanley et al. |

(Continued)

FOREIGN PATENT DOCUMENTS

| | | |
|---|---|---|
| WO | WO 2014/113813 A1 | 7/2014 |
| WO | WO 2015/003133 A1 | 1/2015 |

OTHER PUBLICATIONS

Great Lakes Neurotechnologies, Press Release "Great Lakes Neurotechnologies Awarded Patent for Sensor Based Continuous Parkinsons Assessment During Daily Activities", Dec. 3, 2013, 2 pages www.glneurotech.com.

(Continued)

*Primary Examiner* — Ryan D Walsh
(74) *Attorney, Agent, or Firm* — Christensen O'Connor Johnson Kindness PLLC

(57) ABSTRACT

Techniques and methods for evaluating an instance of a pre-defined task being performed by a user with a handheld tool. In an embodiment, measurement information is stored to a log based on sensor data generated during motion of the handheld tool. Based on a definition of a task and the logged measurement information, a determination is made as to whether the sensed motion corresponds to a performance of at least some action of the defined task. In another embodiment, the definition of the task includes or otherwise corresponds to criteria information. The performance of the task is evaluated based on the criteria information to detect bradykinesia or some other unintentional muscle performance of the user.

20 Claims, 6 Drawing Sheets

(56) References Cited

U.S. PATENT DOCUMENTS

| | | | |
|---|---|---|---|
| 8,308,664 | B2 | 11/2012 | Pathak et al. |
| 2003/0006357 | A1 | 1/2003 | Kaiser et al. |
| 2003/0036805 | A1 | 2/2003 | Senior |
| 2003/0209678 | A1 | 11/2003 | Pease |
| 2009/0173351 | A1 | 7/2009 | Sahin et al. |
| 2009/0227925 | A1 | 9/2009 | McBean et al. |
| 2009/0276058 | A1 | 11/2009 | Ueda et al. |
| 2010/0036384 | A1 | 2/2010 | Gorek et al. |
| 2010/0130873 | A1 | 5/2010 | Yuen et al. |
| 2010/0198362 | A1 | 8/2010 | Puchhammer |
| 2010/0228362 | A1 | 9/2010 | Pathak et al. |
| 2010/0274365 | A1 | 10/2010 | Evans et al. |
| 2013/0123666 | A1 | 5/2013 | Giuffrida et al. |
| 2013/0123684 | A1 | 5/2013 | Giuffrida et al. |
| 2013/0297022 | A1 | 11/2013 | Pathak |
| 2014/0052275 | A1 | 2/2014 | Pathak |
| 2014/0074179 | A1* | 3/2014 | Heldman ............. A61B 5/4082 607/45 |
| 2014/0171834 | A1 | 6/2014 | DeGoede et al. |
| 2014/0257047 | A1 | 9/2014 | Sillay et al. |
| 2014/0257141 | A1 | 9/2014 | Giuffrida et al. |
| 2014/0303605 | A1 | 10/2014 | Boyden et al. |
| 2014/0303660 | A1 | 10/2014 | Boyden et al. |
| 2015/0019135 | A1* | 1/2015 | Kacyvenski ......... A61B 5/0488 702/19 |

OTHER PUBLICATIONS

Pedley, Mark, "Tilt Sensing Using a Three-Axis Accelerometer", Freescale Semiconductor, Inc. Application Note, Document No. AN3461, Rev. 6, Mar. 2013, 22 pages.
Wireless & Mobile Human Monitoring, Latency Tech Note—Wireless Physiological Monitoring, Motion Sensor Latencies for Software Development, 4 pages retrieved from internet Feb. 3, 2015, http://glneurotech.com/bioradio/latency-tech-note/.
Wireless & Mobile Human Monitoring, Wireless motion sensor for 3D data acquisition via Bluetooth technology, Wireless Motion Sensor, 3 pages retrieved from internet Feb. 3, 2015, http://glneurotech.com/bioradio/physiological-signal-monitoring/wireless-motion-sensor/.
Sharon Smaga, "Tremor", American Family Physician, vol. 68, No. 8, Oct. 15, 2003, p. 1545-1552.
Louis, E.D., et al., "How common is the most common adult movement disorder" estimates of the prevalence of essential tremor throughout the world, Movement Disorders, 1998, 2 pages.
Louis, E.D., et al., "Correlates of Functional Disability in Essential Tremor", Movement Disorders, vol. 16, No. 5, 2001, pp. 914-920.
Diamond, A., et al., "The effect of deep brain stimulation on quality of life in movement disorders", Journal of Neurology, Neurosurgery & Psychiatry, 2005, 76(9): p. 1188-1193.
Ahmad Anouti, et al., "Tremor Disorders Diagnosis and Management", Western Journal of Medicine, 1995, 162(6): p. 510-513.
National Parkinson Foundation, Treatment options, 2009, <http://www.parkinson.org/Parkinson-s-Disease/Treatment >1 page.
E. Rocon, et al., "Theoretical Control Discussion on Tremor Suppression via Biomechanical Loading", 2003, 5 pages.
Caroline GL Cao, et al., "Robotics in Healthcare: HF Issues in Surgery," 2007, Online paper, http://ase.tufls.edu/mechanical/EREL/Publications/D-4.pdf, 33 pages.
Rubia P Meshack, et al., "A randomized controlled trial of the effects of weights on amplitude and frequency of postural hand tremor in people with Parkinson's disease", Clinical Rehabilitation, 2002, 16(5): p. 481-492.
Mario Manto, et al., "Dynamically Responsive Intervention for Tremor Suppression", IEEE Engineering in Medicine and Biology Magazine, 2003, 22(3): p. 120-132.
Eduardo Rocon, et al., "Mechanical suppression of essential tremor", The Cerebellum, 2007, 6(1): p. 73-78.
E. Rocon, et al., "Rehabilitation Robotics: a Wearable Exo-Skeleton for Tremor Assessment and Suppression", Proceedings of the 2005 IEEE International Conference on Robotics and Automation, 2005, p. 2271-2276.
Mark Heath, et al., "Design Considerations in Active Orthoses for Tremor Suppression: Ergonomic Aspects and Integration of Enabling Technologies", Assistive Technology—Shaping the Future AAATE, 2003, p. 842-846.
Olivier W. Bertacchini, et al., "Fatigue life characterization of shape memory alloys undergoing thermomechanical cyclic loading", Smart Structures and Materials 2003, 2003. 5053: p. 612-624.
DC-Micromotors, Application Datasheet, 0615 4.5S. 2010; 1 page available from: http://www.micromo.com.
Rodger J. Elble, "Physiologic and essential tremor", Neurology, 1986, 36(2): p. 225-231.
Cameron N. Riviere, et al., "Toward Active Tremor Canceling in Handheld Microsurgical Instruments", IEEE Transactions on Robotics and Automation, vol. 19, No. 5, Oct. 2003, p. 793-800.
Mitchell F. Brin, et al., "Epidemiology and Genetics of Essential Tremor", Movement Disorders, 1998. 13(S3): p. 55-63.
Rodger J. Elble, et al., "Essential tremor frequency decreases with time", Neurology, 2000, 55(10): p. 1547-1551.
Pathak et al. "Dynamic characterization and single-frequency cancellation performance of SMASH (SMA actuated stabilizing handgrip)." In: Modeling, Signal Processing, and Control for Smart Structures, Proceedings of SPIE, vol. 6926, 2008, pp. 692602-1 through 692602-12 [online]. Retrieved on Nov. 26, 2012 (Nov. 26, 2012). Retrieved from the Internet at URL:<http://144.206.159.178/ft/CONF/16413457/16413459.pdf>, entire document.
Shaw et al. "A reduced-order thermomechanical model and analytical solution for uniaxial shape memory alloy wire actuators." In: Smart Materials and Structures, vol. 18, 2009, pp. 1-21 [online]. Retrieved on Nov. 26, 2012 (Nov. 26, 2012). Retrieved from the Internet at URL:<hltp://deepblue.lib.umich.edu/bitstream/2027.42/65088/2/sms9_6_065001.pdf>, entire document, especially Fig. 1b; p. 3, col. 1.
Pathak, A. et al. "A Noninvasive Handheld Assistive Device to Accommodate Essential Tremor: A Pilot Study," Brief Report, Movement Disorders, May 2014; 29(6):838-42. doi: 10.1002/mds.25796.
Pathak, A. et al., "Handheld Tool for Leveling Uncoordinated Motion" U.S. Appl. No. 14/668,516, filed Mar. 25, 2015, whole document.
Salarian, A. et al. "Quantification of Tremor and Bradykinesia in Parkinson's Disease Using a Novel Ambulatory Monitoring System," IEEE Transactions on Biomedical Engineering, vol. 54, No. 2, Feb. 2007, pp. 313-322.

* cited by examiner

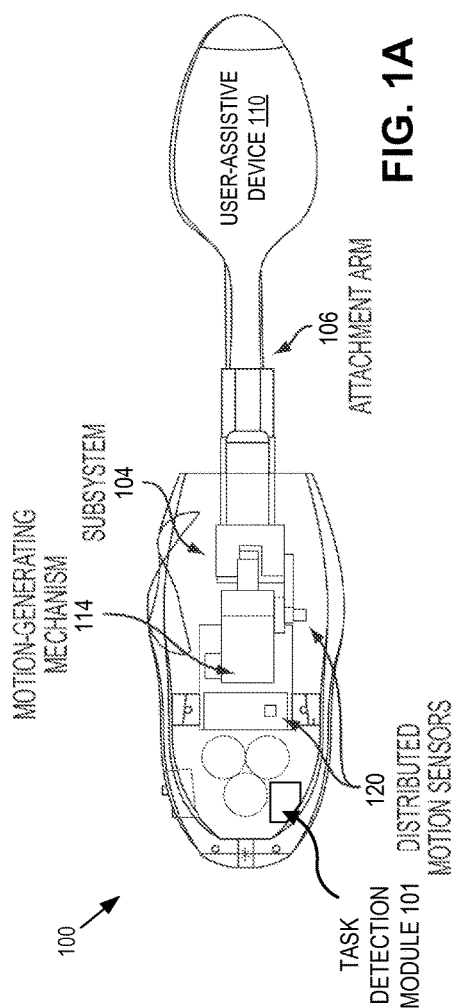
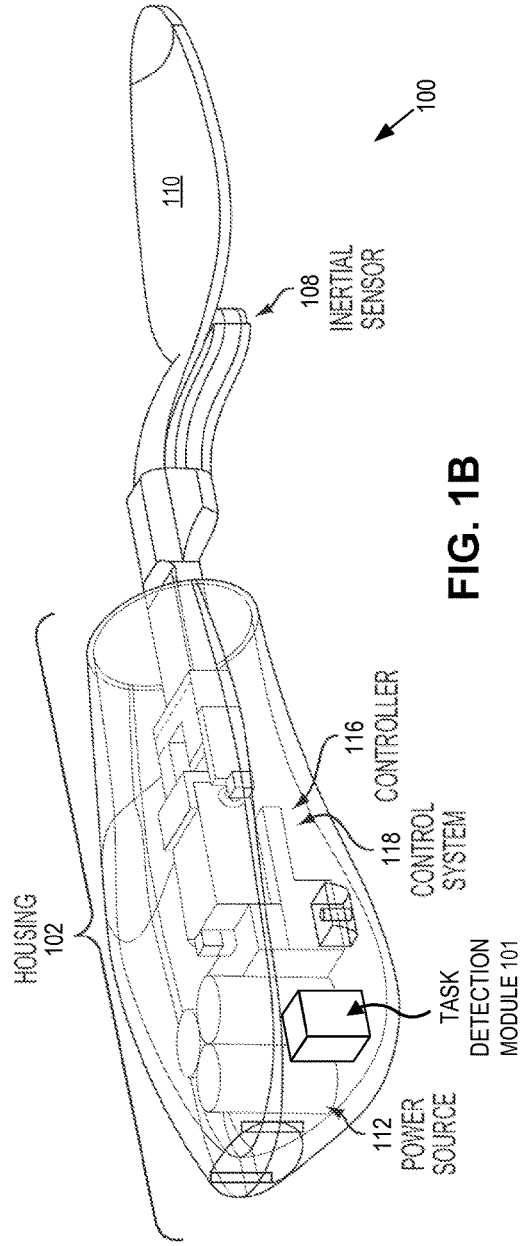

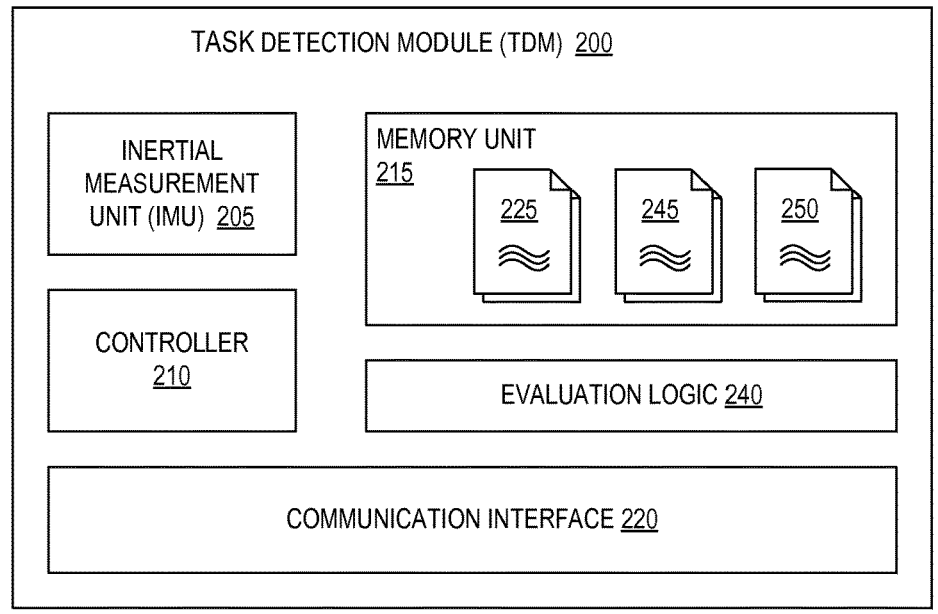
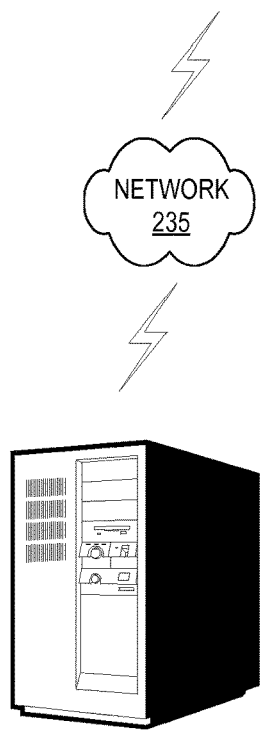
FIG. 2

US 10,159,432 B1

DETECTION AND EVALUATION OF TASK PERFORMANCE WITH A HANDHELD TOOL

BACKGROUND

1. Technical Field

This disclosure relates generally to unintentional muscle performance during use of a tool, and in particular but not exclusively, relates to the detection and evaluation of a task performed with a tool.

2. Background Art

Movement disorders are often caused by chronic neurodegenerative diseases such as Parkinson's Disease ("PD") and Essential Tremor ("ET"). Both of these conditions are currently incurable and can cause unintentional muscle movements or human tremors. Bradykinesia—a type of hypokinesia—is the most characteristic clinical feature of Parkinson's disease, for example, and (in contrast to tremor) is present in basically all cases of Parkinson's disease. Many movement disorders can be severe enough to cause a significant degradation in quality of life, interfering with daily activities/tasks such as eating, drinking, or writing.

Currently, the diagnosing of movement disorders relies on a clinician subjectively and qualitatively assessing an individual using the Fahn-Tolosa-Marin Tremor Rating Scale, the Unified Parkinson Disease (UPDRS) rating scale or other such clinical scale system. Such assessment requires a clinical visit that, due to its subjective nature during a brief period of time, is often prone to errors or intra-clinician variability. Symptom severity at home is typically evaluated from the patient's self-reporting, which is also highly subjective and prone to error. This creates significant challenges when developing and evaluating long-term treatments or interventions for these diseases.

BRIEF DESCRIPTION OF THE DRAWINGS

The various embodiments of the present invention are illustrated by way of example, and not by way of limitation, in the figures of the accompanying drawings and in which:

FIG. 1A is a cross-sectional illustration of a handheld tool that evaluates performance of a task, in accordance with an embodiment of the disclosure.

FIG. 1B is a perspective view illustration of the handheld tool that evaluates performance of a task, in accordance with an embodiment of the disclosure.

FIG. 2 is a functional block diagram illustrating a module to detect and evaluate task performance, in accordance with an embodiment of the disclosure.

DETAILED DESCRIPTION

Figure 3:
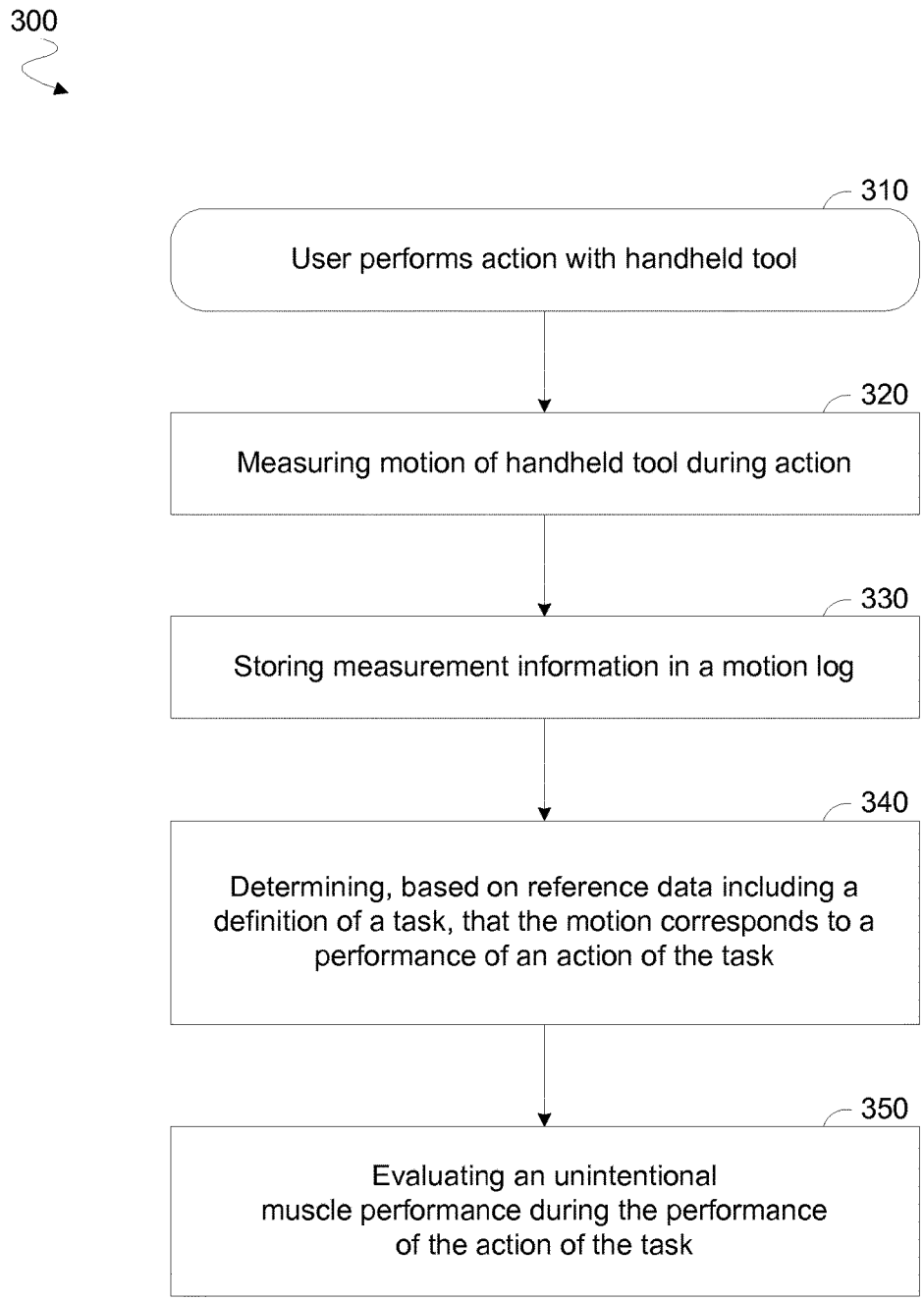
FIG. 3 is a flow chart illustrating a process to evaluate a user's performance of a task using a handheld tool, in accordance with an embodiment of the disclosure.

Embodiments of an apparatus, system and process for detecting and analyzing performance of a pre-defined task by a user while using a handheld tool are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Certain embodiments variously detect an instance of a task being performed, where such detection is based on both sensor data generated with a handheld tool and reference information that, for example, describes one or more actions of the task. Based on processing of the sensor data, motion analysis information may be generated and evaluated, based on criteria information corresponding to a definition of a task, to provide a clinical evaluation of the user—e.g., wherein the information indicates bradykinesia, tremor and/or any of various other conditions that affect muscle performance. In some embodiments, the motion analysis information may be used in a learning algorithm to improve operation of the handheld tool by the user.

FIGS. 1A and 1B illustrate a handheld tool 100 that, in accordance with an embodiment of the disclosure, detects an instance of a pre-defined task being performed and, in some embodiments, further evaluates unintentional muscle performance that has occurred during the instance. Such unintentional muscle performance may include, for example, prohibited or otherwise retarded motion (e.g., bradykinesia, catalepsy), spasms and/or any of various types of tremor motion. FIG. 1A is a cross-sectional illustration of handheld tool 100 while FIG. 1B is a perspective view illustration of the same. Handheld tool 100 may also be capable of detecting and compensating for unintentional muscle movement (tremors); however, it should be appreciated that various embodiments need not include the mechanisms and associated sensors for tremor compensation, even though both features are incorporated into the illustrated embodiment of handheld tool 100. Accordingly, the illustrated embodiment of handheld tool 100 may include a subsystem for detecting performance of a pre-defined task (e.g., a task detection module) and a subsystem for detecting and compensating for tremors. These subsystems may have distinct components, or share some components such as power systems, memory, a controller, and may even share one or more sensors. In some embodiments, some or all components of a subsystem to compensate for tremors may be omitted.

Handheld tool 100 may include a housing 102, which functions as a handle for holding handheld tool 100. Handheld tool 100 may also include an attachment arm 106 coupled to the housing 102. Attachment arm 106 is configured to accept a user-assistive device 110 (e.g., a spoon in the illustrated embodiment) to its end distal from housing 102. In another embodiment, a user-assistive device is integrated with or otherwise permanently attached to housing 102. For example, attachment arm 106 may alternatively be integrated with a specific type of user-assistive device 110 (spoon illustrated). In other embodiments, attachment arm 106 can variously receive one or more different user-assistive devices 110 in a variety of ways including but not limited to a friction, snap, or other form of locking mechanism.

Handheld tool 100 may further include a task detection module ("TDM") 101 for measuring motion and evaluating whether such motion is indicative of an instance of a pre-defined task being performed. Such a task may be pre-defined at least insofar as it is described, prior to such an instance, by reference information that is to be accessed for evaluation of the measured motion. One or more components of TDM 101 may be rigidly attached to housing 102 to measure and track motion (e.g., including measuring lack of motion) of the handle that the user holds. FIGS. 1A and 1B illustrate TDM 101 as a single block within housing 102; however, in other embodiments, TDM 101 includes several functional items that may assume a variety of different form factors and may further be spread throughout housing 102.

The illustrated embodiment of handheld tool 100 further includes a subsystem 104 to detect motion of user-assistive device 110. In the illustrated embodiment, subsystem 104 includes at least one inertial sensor 108 placed, for example, along attachment arm 106 to measure absolute movement of attachment arm 106 and user-assistive device 110. Subsystem 104 may further include a portable power source 112, a control system 118, and at least one distributed motion sensor 120 for measuring motion of attachment arm 106—e.g., relative to housing 102. Portable power source 112 may utilize a variety of options including but not limited to a rechargeable battery, a solar panel, etc. As mentioned above, TDM 101 may share one or more of the components of subsystem 104 (e.g., power source 112, controller 116, etc.). In the illustrated embodiment of handheld tool 100, subsystem 104 further comprises a motion-generating mechanism 114 to compensate for user tremors. However, in other embodiments, one or more of the components of subsystem 104 to compensate tremor motions may also be omitted (e.g., controller 116, motion-generating mechanism 114, etc.) while still implementing the task detection and evaluation functionality disclosed herein.

Sensors of handheld tool 100—e.g., including the illustrative at least one inertial sensor 108 and at least one distributed motion sensor 120—may variously generate sensor data indicating motion of handheld tool 100 by a user. In one embodiment, the at least one inertial sensor 108 is a sensor including but not limited to an accelerometer, gyroscope, or combination of the two. In one embodiment, the at least one distributed motion sensor 120 is a contactless position sensor including but not limited to a hall-effect magnetic sensor. However, the particular number, positioning and/or types of such sensors is not limiting on some embodiments.

To detect motion according to an embodiment, a dynamic (including a position and/or an orientation) of user-assistive device 110 may be sensed—e.g., relative to some reference dynamic. For this sensing, the at least one inertial sensor 108 may be placed along the attachment arm 106 and may be used to measure the absolute motion of the user-assistive device 110 while providing low noise and sufficient sensitivity for the application. The direct sensor placement of the at least one inertial sensor 108 along attachment arm 106 may give a unique advantage to handheld tool 100 as it is extremely robust and does not rely on inverse kinematics/dynamics which may change depending on usage. Thus, a variety of objects can be used to implement user-assistive device 110 without the need to pre-determine and pre-program the length and weight of user-assistive device 110 into the controller 116.

In the illustrated embodiment, the at least one distributed motion sensor 120 is located within the housing 102 which is located at the base of the handheld tool 100. The at least one distributed motion sensor 120 may measure the relative motion of attachment arm 106 relative to the housing 102, wherein user-assistive device 110 is kept at a center position relative to housing 102. In one embodiment, the at least one distributed motion sensor 120 is at least one contactless hall-effect position sensor that provides angular feedback for control system 118 and relies on a changing magnetic field that is dependent on the actuation angle. The changing magnetic field may be detected by a strategically placed integrated circuit (IC) located within the at least one distributed motion sensor 120, whose analog output may provide a completely non-contact angular detection that is capable of withstanding a large number of cycles. The at least one distributed motion sensor 120, with its contactless sensing methods, may provide improved reliability over conventional direct-contact sensing methods such as potentiometers that wear over time.

Information representing the sensed motion of handheld tool 100 may be provided by the sensors directly or indirectly to TDM 101—e.g., via control system 118—for processing to determine whether such motion constitutes an instance of the user performing a pre-defined task. For example, TDM 101 may include or otherwise have access to a memory (not shown) storing reference information that includes respective definitions of one or more tasks. In an embodiment, a task definition describes one or more actions of the task—e.g., where such an action is described with respect to motion of the handheld tool 100. Based on sensor data and a task definition, TDM 101 may perform processing to determine whether a detected motion of handheld tool 100 qualifies (e.g., according to some pre-defined criteria) as being an instance of an action (or actions) of the defined task. In some embodiments, one or more sensors for sensing motion of handheld tool 100 are incorporated into TDM 101—e.g., as part of an inertial measurement unit (not shown) of TDM 101.

In an embodiment where tremor compensation functionality is provided, control system 118 may send voltage commands, in response to sensors 118, 120, to motion-generating mechanism 114 through controller 116 to cancel or otherwise mitigate the user's tremors or unintentional muscle movements. This cancellation may maintain and stabilize a position of the user-assistive device 110, keeping it centered relative to the housing 102. In one embodiment, controller 116 comprises an electrical system capable of producing an electrical response from sensor inputs such as a programmable microcontroller a field-programmable gate array (FPGA), an application specific integrated circuit ("ASIC"), or otherwise. In one embodiment, the control system 118 is a closed-loop control system that senses motion and acceleration at various points along handheld tool 100 and feeds detailed information into a control algorithm that moves motion-generating mechanism 114 appropriately to cancel the net effect of a user's unintentional muscle movements and thus stabilize the position of user-assistive device 110.

One of ordinary skill in the art will readily recognize that an apparatus, a system, or method as described herein may be utilized for a variety of applications. For example, various different user-assistive devices 110 may include a manufacturing tool, a surgical tool, a kitchen utensil (e.g., fork, knife, spoon), a sporting tool, a yard tool, a grooming tool (e.g., comb, nail clippers, tweezers, make-up applicator, etc.), or a dental hygiene tool (e.g., toothbrush, flossing tool, etc.). Thus, handheld tool 100 may be useful in improving the quality of life for the multitudes of individuals suffering from neurological motion disorders.

FIG. 2 is a functional block diagram illustrating a task detection module TDM 200, in accordance with an embodiment of the disclosure. TDM 200 is one possible implementation of TDM 101 illustrated in FIGS. 1A and 1B. The illustrated embodiment of TDM 200 includes an inertial measurement unit ("IMU") 205, a controller 210, a memory unit 215, a communication interface 220 and evaluation logic 240.

IMU 205 may be disposed in rigid contact with housing 102 (or other such handle structure) to directly measure motion of a handle and by extension the motions of a user's hand. TDM 200 facilitates the measurement of human motion while a user is performing an everyday task, such as eating, brushing teeth or grooming (e.g., applying makeup). This is an important distinction over conventional in-clinic evaluations that subjectively assess the motion of a hand while a patient is attempting to perform a task in a time-limited and artificial environment. Measurement and tracking of motion while the patient is performing an everyday task measures the condition under real-world scenarios that are most adversely impacted by neurological conditions. Accordingly, TDM 200 may be embedded within everyday items or tools that are used routinely by patients to accurately measure and track their condition. This can lead to improved evaluations.

Not only can handheld tool 100 measure and track human motion during a routine task, but it can conveniently do so over a period of time to obtain a more reliable dataset for statistical analysis. Furthermore, handheld tool 100 can be used at home where the user is more relaxed and under less stress than a formal evaluation in a practitioner's office. Data collection within the home environment along with larger datasets than can be obtained in-clinic, can provide more reliable data for evaluation of a patient's symptoms. Improved evaluation and diagnosis of a patient's movement disorder facilitate improved treatments and interventions of the various diseases and the conditions that cause human movement disorders.

IMU 205 may couple to, and/or be implemented using, any of a variety of devices that measure motions of the handle of handheld tool 100. For example, IMU 205 may include (or alternatively, be coupled to receive data from) one or more accelerometers that measure linear accelerations. In one embodiment, IMU 205 includes, or receives sensor data from. accelerometers capable of measuring translational accelerations of the handle in three orthogonal dimensions (e.g., x, y, and z dimensions). In one embodiment, IMU 205 includes or is coupled to a gyroscope to measure rotational motions (e.g., angular velocity about an axis) of the handle of handheld tool 100. In various embodiments, the gyroscope may be capable of measuring the rotational motions about one, two, or three orthogonal rotational axes. In one embodiment, IMU 205 includes or couples to a magnetometer to measure motions of the handle relative to a magnetic field (e.g., Earth's magnetic field or other externally applied magnetic field). In various embodiments, IMU 205 may include various combinations of some or all of the above listed motion measuring devices. Furthermore, these motion sensors may be disposed together on a common substrate that is rigidly attached to housing 102, or disposed throughout housing 102.

Controller 210 may be communicatively coupled to IMU 205 and memory unit 215 to read motion data output from IMU 205 and store the motion data into memory unit 215. The motion data may be collected over a period of time. For example, the motion data may be collected while the user performs an individual task—e.g., repeatedly over the course of an hour, a day, a week, or other period of time. The collected motion data stored in memory unit 215 may form a motion log 225. In one embodiment, motion log 225 may contain enough information about the user's motions (linear accelerations, rotational velocities, durations of these accelerations/velocities, orientation relative to a magnetic field, etc.), based upon the motion data output from IMU 205, to recreate those motions using motion log 225. In one embodiment, motion log 225 may also record date/time stamps of when various motion data was collected.

Information in motion log 225 may be evaluated, based on reference data, to determine whether a motion represented by such information corresponds to a performance of some action of a pre-defined task. TDM 200 may include or otherwise have access to reference data 245—e.g., in memory unit 215—that includes respective definitions of one or more tasks. An evaluation based on motion log 225 and reference data 245 may be performed—e.g., by evaluation logic 240 of TDM 200—to determine whether a motion detected by IMU 205 meets some pre-defined test criteria to qualify as an instance of at least some action of a defined task. For example, the task definition may identify one or more characteristics of an action, where evaluation logic 240—e.g., including hardware, firmware and/or executing software—calculates some metric of conformity to the one or more characteristics. Such a metric may be compared to a threshold level of conformity, where based on such comparison, evaluation logic 240 signals that an instance of the action being performed is indicated. In an embodiment, evaluation logic 240 (or other logic responsive thereto) may perform further calculations to quantify some unintentional muscle performance during the instance of the task.

In some embodiments, identifying of an instance of a task being performed is further based on context information (not shown)—e.g., other than information specifying a position, an orientation or a motion of the tool including TDM 200—that is included in memory unit 215 or is otherwise available to evaluation logic 240. By way of illustration and not limitation, such context information may identify where (e.g., in a particular room or other geographic location) and/or when (e.g., at a particular date, day of the week and/or time of day) a particular task can be expected to be performed. Alternatively or in addition, such context information may include user profile information describing a history of previous performances of one or more tasks by the user. In some embodiments, context information identifies a particular type of user-assistive device 110 that was attached to the handheld 100 when the motion data was collected. Alternatively or in addition, context information may include or otherwise be based on an input from a user explicitly specifying that the task has been, is being or will be performed. Context information may describe other conditions that are identified as typically coinciding with or otherwise correlating to performance of a task—e.g., where such characteristics include a force imparted by the user on the distal end of the device, a pressure of the user's grip on housing 102, biometric information (e.g., describing the user's respiration) and/or any of a variety of other conditions. Certain embodiments are not limited with respect to a particular source of and/or delivery mechanism for such context information, which may be provided, for example, as an a priori input to TDM 200.

Such context information may directly or indirectly provide an indication of an action of a task (e.g., eating with a fork, knife, or spoon, etc.) being performed by the user when motion data was collected. For example, based on a context that coincides with motion detected by IMU 205, evaluation logic 240 may identify a task (or a particular action of a task) as being more closely associated with the context—e.g., as compared to some other task or action of a task. In response, evaluation logic 240 may select or otherwise identify such a task (or action thereof) as being more likely to correspond to the motion coinciding with the context.

Controller 210 and/or evaluation logic 240 may be implemented with a programmable microcontroller, a FPGA, an ASIC or other devices capable of executing logical instructions. The logical instructions themselves may be hardware logic, software logic (e.g., stored within memory unit 215 or elsewhere), or a combination of both. Memory unit 215 may be implemented using volatile or non-volatile memory (e.g., flash memory), in one embodiment.

Communication interface 220 may be communicatively coupled to output the motion log 225 from memory unit 215 to remote server 230 via network 235 (e.g., the Internet). In one embodiment, communication interface 220 is a wireless communication interface (e.g., Bluetooth, WiFi, etc.). For example, communication interface 220 may establish a wireless link to a user's cellular phone which delivers, to server 230 via an installed task detection and evaluation application, motion log 225 and/or evaluation results—e.g., the illustrative evaluation data 250—generated based on motion log 225 and reference information 245. The application may enable the user to control privacy settings, add comments about their usage of handheld tool 100, setup automatic periodic reporting of data, initiate a one-time reporting of data, along with other user functions. In yet another embodiment, communication interface 220 may be a wired communication port (e.g., USB port). For example, when the user connects handheld tool 100 to a charging dock to charge power source 112, communication interface 220 may also establish a communication session with remote server 230 for delivery of motion log 225 thereto.

In the illustrative embodiment of FIG. 2, evaluation logic 240 and reference data 245 are features local to TDM 200. However, in another embodiment, evaluation logic 240 and reference data 245 instead reside in server 230 or some other device that is remote from a handheld tool which includes TDM 200. For example, TDM 200 may provide motion log 225 via network 235, where processing of the data of motion log 225 is performed to determine, remotely from TDM 200, whether a pre-defined task was performed with a handheld tool that includes TDM 200. Alternatively or in addition, such processing may quantify, remotely from TDM 200, some unintentional muscle performance during an instance of a task (e.g., where the task is identified at TDM 200).

FIG. 3 illustrates features of a method 300 for detecting and evaluating performance of a task with a handheld tool according to an embodiment. Method 300 may be performed based on sensor data generated with the handheld tool (such as handheld tool 100)—e.g., where the sensor data is generated while, at 310, a user performs an action with the handheld tool. In certain embodiments, at least some of method 300 is performed by a computer device (e.g., server 230) that is remote from such a handheld tool, based on sensor data generated by the handheld tool.

Method 300 may include, at 320, measuring motion of the handheld tool—e.g., where such measuring is performed by IMU 205 based on an output from one or more sensor mechanisms of the handheld tool such as the at least one inertial sensor 108 and/or the at least one distributed motion sensor 120. Method may further comprise, at 330, storing in a motion log—e.g., of the handheld tool—measurement information that is based on the measuring at 320. In an embodiment, the storing at 330 includes storing data identifying one or more positions, orientations, rates of change thereof (e.g., first order, second order or the like) and/or other dynamics information about the handheld tool. The storing at 330 may further include writing respective timestamp values for various dynamics information.

Figure 4:
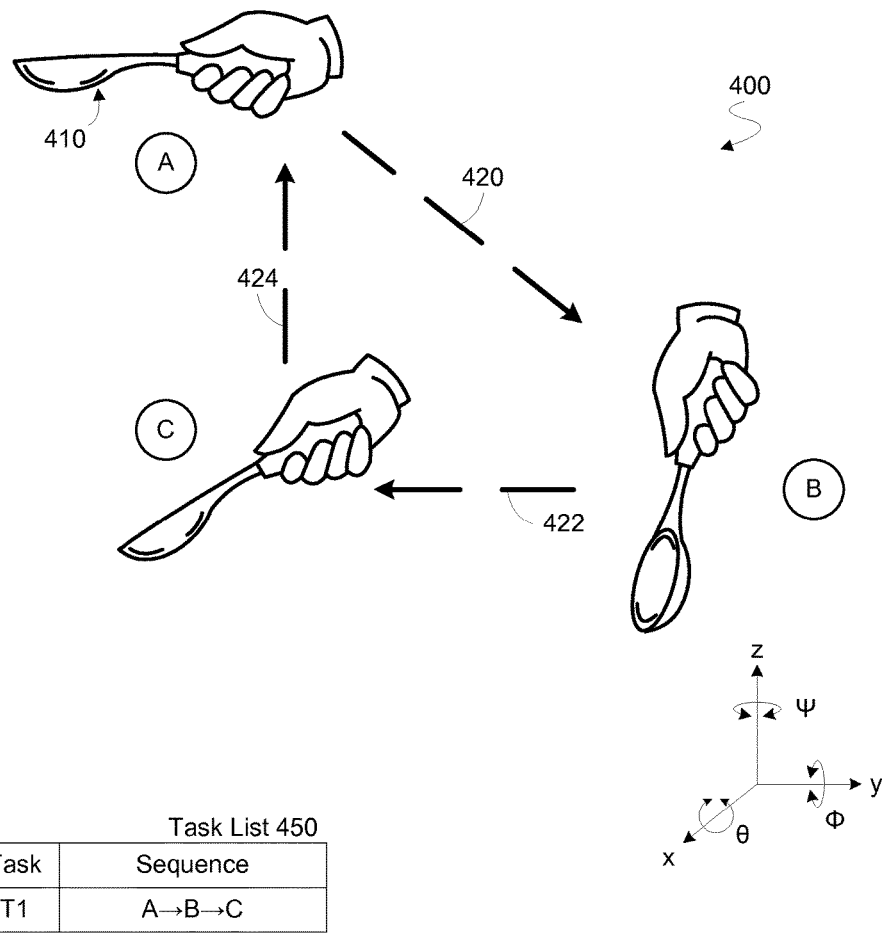
FIG. 4 shows reference information for use in evaluating, according to an embodiment of the disclosure, the performance of a task with a handheld tool.

In an embodiment, method 300 further comprises, at 340, determining that the motion measured at 320 corresponds to a performance of an action of a task. The determining at 340 may be based at least in part on reference data including a definition of the task. For example, reference information may define one or more tasks such as an eating task, a drinking task, a hygiene task (e.g., brushing teeth), a grooming task (e.g., brushing hair) and/or any of a variety of other everyday tasks. By way of illustration and not limitation, FIG. 4 illustrates a performance 400 of an eating task with a handheld tool 410 (such as handheld tool 100, for example), where performance 400 is evaluated with handheld tool 410, according to an embodiment, based on a task definition for the eating task.

A task definition may be provided as a priori reference information, for example. In some embodiment, the handheld tool (or alternatively, a device remote from the handheld tool) is programmed with a task definition by a clinician, remote service or other external agent. Such a task definition may serve as a baseline for evaluating actual performance of one or more instances of the task—e.g., where the evaluating is further based on measurement information (such as that stored at 330) describing such actual performance. The task definition may be determined based at least in part on statistical studies of a population, on evaluation of the user in a clinic setting, on previous calibration of the handheld tool during performance of the task and/or the like. Certain embodiments are not limited with respect to a particular source of a task definition or a particular mechanism for communicating the task definition.

A task definition may define or otherwise indicate one or more actions of the task—e.g., where the task definition indicates that a task is to include actions performed according to a particular sequence. By way of illustration and not limitation, reference information defining one or more tasks performed with handheld tool 410 may include an entry of a task list 450 that identifies the eating task as T1 and that defines a sequence of states A, B, C that are to comprise T1. In such an embodiment, actions of task T1 may include a transition A→B 420 from state A to state B, a transition B→C 422 from state B to state C and a transition C→A 424 from state C back to state A. Such states A, B, C may each include a respective dynamic (e.g., a position and/or orientation) of handheld tool 410. For example, a table 460 of the reference information may define, for each of states A, B, C, respective orientations (e.g., including some or all of a roll, pitch and yaw) of handheld tool 410 during that state. Alternatively or in addition, a table 470 of the reference information may define, for each of transitions A→B 420, B→C 422 and C→A 424, a respective distance or distances traveled (e.g., in an x, y, z coordinate system) by handheld tool 410 during that transition.

Although some embodiments are not limited in this regard, some or all dynamics may be defined by tables 460, 470 in relative terms—e.g., independent of an unchanging reference location and/or an unchanging reference orientation. For example, an IMU of handheld tool 410 may occasionally perform calibration/orientation calculations to update some reference dynamic that is to serve as, or otherwise be used to determine, one of states A, B, C. Such a reference dynamic may be updated, in an embodiment, based at least in part on detection that the user changed an average direction of motion of handheld tool 410, maintained handheld tool 410 below some threshold amount of movement for at least some threshold period of time, and/or the like. In response to such detection, TDM 200 (or other such logic of the handheld tool) may set a new reference location and/or a new reference orientation to be used in task detection/evaluation for subsequent motion of the handheld tool.

The definition of task T1, or other such task, may further comprise or otherwise correspond to information (not shown)—referred to herein as "tolerance information"—that specifies or otherwise indicates an amount of deviation from the defined task, or from a particular action of such a task, that is acceptable (or unacceptable) for being considered as part of performance of the task/action. For example, table 460, 470 may further specify marginal variation that is acceptable for some or all of roll values $\theta_a$, $\theta_b$, $\theta_c$, pitch values $\Phi_a$, $\Phi_b$, $\Phi_c$ and yaw values $\Psi_a$, $\Psi_b$, $\Psi_c$. Alternatively or in addition, table 470 may further specify marginal variation that is acceptable for some or all of x-dimension distances $x_{ab}$, $x_{bc}$, $x_{ca}$, y-dimension distances $y_{ab}$, $y_{bc}$, $y_{ca}$ and z-dimension distances $Z_{ab}$, $Z_{bc}$, $Z_{ca}$. Such tolerance information may be provided a priori by a clinician or other remote agent—e.g., where the tolerance information is determined based at least in part on population statistics, evaluation of the user in a clinic setting and/or the like.

Referring again to FIG. 3, method 300 may further comprise, at 350, evaluating an unintentional muscle performance during the performance of the action of the task. In an embodiment, a task definition includes or otherwise corresponds to information—referred to herein as "criteria information"—that specifies or otherwise indicates some threshold for identifying muscle performance as being unintentional (or alternatively, intentional) muscle performance. Such criteria information may specify or otherwise indicate a threshold level of a metric used to evaluate user motion—e.g., where a value of the metric is evaluated for the user and compared to the threshold level to determine whether some clinical condition is indicated. The criteria information may represent a threshold that is specific to the defined task (e.g., specific to an action of that task). For example, a criteria information may include a threshold amount of acceptable (or unacceptable) deviation from a time duration, speed, path, orientation or other characteristic of the task as defined by the reference information. Additionally or alternatively, criteria information may define a threshold deviation that is specific to a particular user of the handheld tool. In an embodiment, determining such criteria information includes methods adapted from conventional techniques for clinically assessing acceptable (or unacceptable) levels of unintentional muscle performance. It is noted that detection of task performance, based on tolerance information for a task definition, may be distinguished from an evaluation, based on criteria information, of unintentional muscle performance during such task performance. For example, criteria information may—as compared to corresponding threshold information—represent a different metric of user motion and/or may represent a higher granularity analysis of a given metric.

In the illustrative example of FIG. 4, criteria information for the defined task T1 includes, in table 470, respective minimum threshold time differences $\Delta$Tmin for some or all of transitions A→B 420, B→C 422 and C→A 424. In such an embodiment, evaluation logic 240 (or other such logic to evaluate task performance) may detect indicia of a muscle disorder based on one or more $\Delta$Tmin values. By way of illustration and not limitation, bradykinesia may be indicated if the transition A→B 420 of performance 400 takes more than a time duration tab, if the transition B→C 422 of performance 400 takes more than a time duration the and/or if the transition C→A 424 of performance 400 takes more than a time duration $t_{ca}$. Criteria information may additionally or alternatively represent a threshold level and/or frequency of tremor, catalepsy, spasticity or any of various other types of unintentional muscle performance during performance of a corresponding task. In an embodiment, criteria information such as the illustrative $\Delta$Tmin values may be used for multiple evaluations each of a different respective instance of a task being performed. Alternatively or in addition, such criteria information may be used to perform a single evaluation of a statistical analysis (e.g., including an average) of multiple instances of such a task being performed.

FIGS. 5A-5D show graphs 500, 510, 520, 530 representing evaluations, each according to a respective embodiment, to detect for unintentional muscle performance during a task. To illustrate certain features of various embodiments, graphs 500, 510 520, 530 are described herein with reference to evaluation of a performance of eating task T1. However, such description may be extended to additionally or alternatively apply to any of a variety of other evaluations to detect unintentional muscle performance by a user of a handheld tool.

Figure 5A:
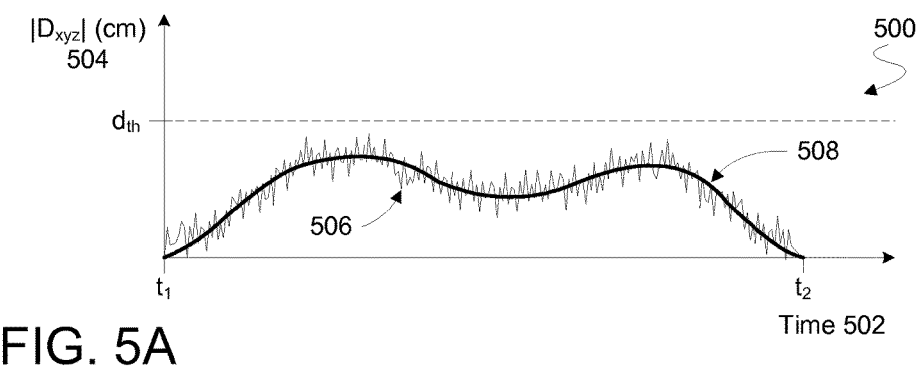
FIGS. 5A-5D are graphs illustrating respective task evaluations performed each according to a corresponding embodiment of the disclosure.

Graph 500 of FIG. 5A includes values over time 502 of a distance $|D_{xyz}|$ 504 of deviation by handheld tool 410 from a path for transition A→B 420—e.g., where the path specified or otherwise indicated by the definition of task T1. Such a path may be a line extending between respective positions defined for states A, B or, in some embodiments, may be some curved path defined for a transition between states A, B. Sensor information may be processed to calculate position information for the handheld tool 410 between a time t1 associated with handheld tool being in state A, and a time t2 associated with handheld tool being in state B. Graph 500 includes a plot 506 of points each representing a respective difference between a position indicated by raw sensor data of the handheld tool and a corresponding closest point of a path between respective positions of states A, B. Evaluation of task performance may include determining whether a degree and/or type of deviation from such a path is characteristic of unintentional muscle performance. By way of illustration and not limitation, the evaluation may include calculating running average values (or other such statistical information) based on points of plot 506—e.g., as represented by the illustrative plot 508. Spasm, seizure or other unintentional muscle performance may be indicated, for example, by some portion of plot 508 (or alternatively, of plot 506) exceeding a threshold level $d_{th}$ of distance $|D_{xyz}|$ 504. Alternatively or in addition, such unintentional muscle performance may be indicated by a total area of the curve under plot 508 (or plot 506) being greater than some maximum allowable threshold. Any of a variety of other test conditions may be used, according to different embodiments, to evaluate muscle performance based on distance $|D_{xyz}|$ 504. The level $d_{th}$ or other such threshold information may be provided, for example, based on a statistical study of a population having a particular muscle disorder, on evaluation of the user in a clinic setting and/or the like.

Figure 5B:
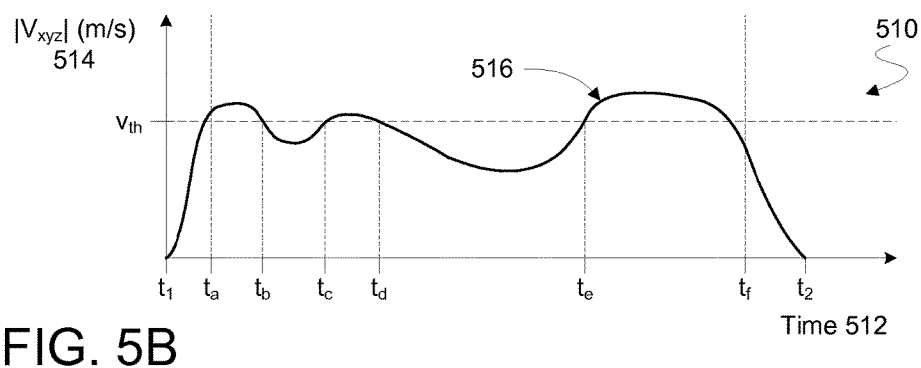

Graph 510 of FIG. 5B shows a plot 516 over time 512 of values—e.g., instantaneous values or moving average values—for a speed $|V_{xyz}|$ 514 of handheld tool 410 during transition A→B 420. Evaluation of task performance between time $t_1$ and time $t_2$ may include determining whether handheld tool 410 drops below some threshold minimum speed—e.g., at least for some threshold period of time. As illustrated by plot 516, bradykinesia (or other such condition) may be indicated by handheld tool 410 dropping below a threshold speed $v_{th}$ between times $t_b$, $t_c$ and also between times $t_d$, $t_e$. In an embodiment, speed $|V_{xyz}|$ 514 may be ignored during some periods of time—e.g., between times $t_1$, $t_a$ when a user is starting movement for transition A→B 420 and/or between times $t_f$, $t_2$ when a user is stopping movement for transition A→B 420.

Figure 5C:
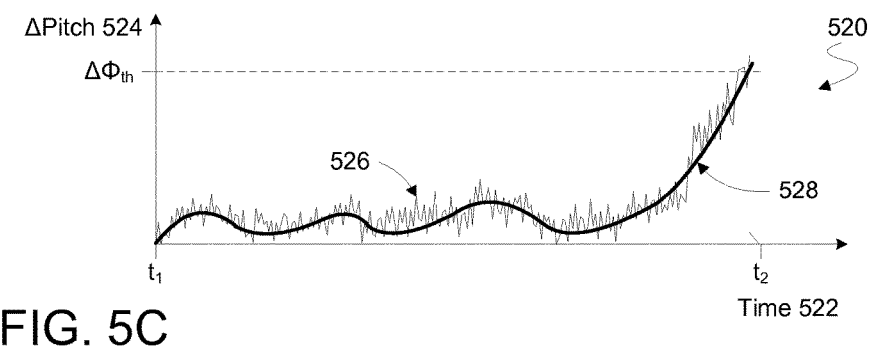

Graph 520 of FIG. 5C includes values over time 522 for a difference (Δ) 524 each between a measured pitch (Φ) of handheld tool 410 and a corresponding one of pitch values variously defined for respective points along the path for transition A→B 420. Graph 520 includes a plot 526 of points, measured between times $t_1$, $t_2$, each representing a respective difference between a pitch indicated by raw sensor data of handheld tool 410 and a pitch value specified by the definition of task T1 for a coinciding closest point of the path for transition A→B 420. Evaluation of task performance may include determining whether an extent of deviation from a defined pitch is characteristic of unintentional muscle performance. By way of illustration and not limitation, moving average calculations, low-pass filtering and/or other processing may be performed on raw sensor data or on the data of plot 526, as represented by the illustrative plot 528. Weak muscle control may be indicated, for example, by some portion of plot 528 (or alternatively, of plot 526) exceeding a threshold pitch difference $\Delta\Phi_{th}$ at some point during the transition A→B 420. The threshold pitch difference $\Delta\Phi_{th}$ or other such threshold information may be provided a priori by a clinician based, for example, on diagnostic methods adapted from conventional techniques. Similar evaluation of unintended muscle performance may be additionally or alternatively be performed based on some or all of pitch, roll and yaw (e.g., including a combination thereof) of a handheld tool, according to different embodiments.

Figure 5D:
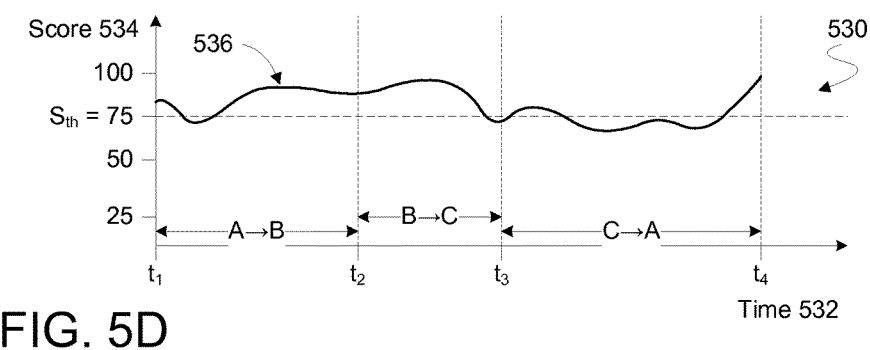

Graph 530 of FIG. 5D shows a plot 536 over time 532 of values for a score 534 representing a metric of a user's intentional muscle performance during one or more instances of task T1 with a handheld tool. Plot 536 includes respective values for transition A→B 420 between times $t_1$, $t_2$, for transition B→C 422 between times $t_2$, $t_3$, and for transition C→A 424 between times $t_3$, $t_4$. Score 532 may be a composite score—e.g., normalized to a scale of 0 to 100—that is calculated based on $|D_{xyz}|$ 504, $|V_{xyz}|$ 514 and/or any of a variety of other metrics of the performance of task T1. Evaluation of unintentional muscle performance may include determining whether score 534 drops below some threshold value $S_{th}$ (e.g., 75) for at least some threshold period of time. In the illustrative embodiment shown, bradykinesia, tremor, spasm and/or other muscular condition may be indicted by consistently low values for score 536 during (for example) transition C→A 424. Determining score 534 and/or threshold value $S_{th}$ include operations adapted from conventional techniques for calculating and evaluating a clinical score of patient movement.

Techniques and architectures for evaluation motion by a user are described herein. Some portions of the detailed description herein are presented in terms of algorithms and symbolic representations of operations on data bits within a computer memory. These algorithmic descriptions and representations are the means used by those skilled in the computing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Certain embodiments also relate to apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs) such as dynamic RAM (DRAM), EPROMs, EEPROMs, magnetic or optical cards, or any type of media suitable for storing electronic instructions, and coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description herein. In addition, certain embodiments are not described with reference to any particular programming language. It will be appreciated that a variety of programming languages may be used to implement the teachings of such embodiments as described herein.

Besides what is described herein, various modifications may be made to the disclosed embodiments and implementations thereof without departing from their scope. Therefore, the illustrations and examples herein should be construed in an illustrative, and not a restrictive sense. The scope of the invention should be measured solely by reference to the claims that follow.

What is claimed is:

1. A tool, comprising:
a handle configured to be held by a hand of a user;
an attachment arm extending from the handle, wherein a distal end of the attachment arm opposite the handle is adapted to couple with a user-assistive device;
an inertial measurement system disposed within the handle to obtain measurements of a motion of the tool representative of a task being performed by the user with the tool, the inertial measurement system including:
one or more accelerometers to measure translational accelerations of the handle in one or more orthogonal dimensions; and
a gyroscope to measure rotational motions of the handle about an axis, wherein the one or more accelerometers and the gyroscope are disposed within the handle, and wherein the measurements of the motion of the tool are provided, at least in part, by the one or more accelerometers and the gyroscope;
a memory coupled to the inertial measurement system to store measurement information based on the measurements of the motion of the tool, wherein the memory includes reference data;
evaluation logic circuitry coupled to the memory, wherein the memory stores instructions that when executed by the evaluation logic circuitry causes the tool to perform operations including:
identifying a task definition included in the reference data as corresponding to the task performed by the user based, at least in part, on context information and an evaluation of the measurement information based on the reference data, wherein the context information indicates a type of the user-assistive device coupled to the attachment arm; and
determining the motion of the tool includes identifying a presence of unintentional muscle movement of the user when the measurement information is outside one or more thresholds included in the task definition; and
a communication interface coupled to the evaluation logic circuitry, the communication interface to output from the tool a signal indicating the unintentional muscle movement.

2. The tool of claim 1, wherein the memory includes additional instructions that when executed by the evaluation logic circuitry causes the tool to perform further operations including:
identifying the unintentional muscle movement as an indication of bradykinesia.

3. The tool of claim 2, wherein the task definition includes a sequence of one or more actions, wherein the memory includes additional instructions that when executed by the evaluation logic circuitry causes the tool to perform further operations including:
identifying a portion of the measurement information as corresponding to at least one of the one or more actions; and
determining the measurement information is outside of the one or more thresholds when a duration of at least the portion is greater than a maximum threshold period of time or a speed of the tool during at least the portion is less than a minimum threshold speed of the tool, wherein the one or more thresholds of the task definition includes at least one of the maximum threshold period of time or the minimum threshold speed of the tool.

4. The tool of claim 1, wherein the task definition includes a sequence of one or more actions, wherein the memory includes additional instructions that when executed by the evaluation logic circuitry causes the tool to perform further operations including:
identifying the measurement information as corresponding to the sequence of one or more actions when the motion of the tool is within a conformity threshold included in the task definition.

5. The tool of claim 1, wherein the task definition includes a sequence of one or more actions, wherein the memory includes additional instructions that when executed by the evaluation logic circuitry causes the tool to perform further operations including:
identifying a portion of the measurement information as corresponding to at least one of the one or more actions; and
determining the measurement information is outside of the one or more thresholds when the portion of the measurement information of the tool deviates beyond a threshold deviation from a path corresponding to the at least one of the one or more actions of the task definition.

6. The tool of claim 1, wherein the context information further identifies at least one of a time, a date, or a geographic location.

7. The tool of claim 1, wherein the context information further identifies a biometric condition of the user.

8. The tool of claim 1, wherein the context information further identifies a grip force imparted on the handle.

9. The tool of claim 1, wherein the user-assistive device comprises a kitchen utensil, and wherein the task definition corresponds to an eating task.

10. The tool of claim 1, wherein the task definition corresponds to a hygiene task.

11. The tool of claim 1, further comprising:
a distributed motion sensor coupled to the handle and the attachment arm, wherein the distributed motion sensor is positioned to measure relative motion of the attachment arm relative to the handle, and wherein the measurement are further provided, at least in part, by the distributed motion sensor.

12. The tool of claim 1, wherein the reference data includes a plurality of task definitions including the task definition, wherein each of the plurality of task definitions corresponds to potential tasks performable by the user with the tool when the user-assistive device is coupled to the attachment arm.

13. The tool of claim 1, wherein the inertial measurement system further includes:
a magnetometer to measure motions of the handle relative to a magnetic field, wherein the measurements of the motion of the tool are further provided, at least in part, by the magnetometer.

14. A method performed by a tool, the method comprising:
measuring a motion of the tool with one or more accelerometers and a gyroscope disposed within a handle of the tool configured to be held by a hand of a user, wherein a distal end of the attachment arm opposite the handle is adapted to couple with a user-assistive device, and wherein the motion of the tool is representative of a task being performed by the user with the tool;

storing, in a memory of the tool, measurement information based on the measuring of the motion of the tool, wherein the memory includes reference data;

identifying, by evaluation logic circuitry, a task definition included in the reference data as corresponding to the task performed by the user based, at least in part, on context information and an evaluation of the measurement information based on the reference data, wherein the context information indicates a type of the user-assistive device coupled to the attachment arm; and determining, by the evaluation logic circuitry, the motion of the tool includes identifying a presence of unintentional muscle movement of the user when the measurement information is outside of one or more thresholds included in the task definition.

15. The method of claim 14, further comprising:

identifying whether the unintentional muscle movement includes an indication of bradykinesia.

16. The method of claim 14, wherein the user-assistive device comprises a kitchen utensil, and wherein the task definition corresponds to an eating task.

17. A non-transitory computer-readable storage medium having stored thereon instructions which, when executed by one or more processing units, cause the one or more processing units to perform a method comprising:

measuring a motion of a tool with one or more accelerometers and a gyroscope disposed within a handle of the tool configured to be held by a hand of a user, wherein a distal end of the attachment arm opposite the handle is adapted to couple with a user-assistive device, and wherein the motion of the tool is representative of a task being performed by the user with the tool;

storing, in a memory of the tool, measurement information based on the measuring of the motion of the tool, wherein the memory includes reference data;

identifying a task definition included in the reference data as corresponding to the task performed by the user based, at least in part, on context information and an evaluation of the measurement information based on the reference data, wherein the context information indicates a type of the user-assistive device coupled to the attachment arm; and determining the motion of the tool includes identifying a presence of unintentional muscle movement of the user when the measurement information is outside of one or more thresholds included in the task definition.

18. The computer-readable storage medium of claim 16 further including:

identifying whether the unintentional muscle movement includes an indication of bradykinesia.

19. The computer-readable storage medium of claim 18, wherein the task definition includes a sequence of one or more actions, wherein the computer-readable storage medium further includes:

identifying a portion of the measurement information as corresponding to at least one of the one or more actions; and determining the measurement information is outside of the one or more threshold when a duration of at least the portion is greater than a maximum threshold period of time or a speed of the tool during at least the portion is less than a minimum threshold speed of the tool, wherein the one or more thresholds of the task definition includes at least one of the maximum threshold period of time or the minimum threshold speed of the tool.

20. The computer-readable storage medium of claim 17, wherein the task definition includes a sequence of one or more actions, wherein the computer-readable storage medium further includes:

identifying the measurement information as corresponding to the sequence of one or more actions when the motion of the tool is within a conformity threshold included in the task definition.

\* \* \* \* \*